United States Patent
Bailey

(10) Patent No.: US 11,622,682 B2
(45) Date of Patent: *Apr. 11, 2023

(54) METHODS AND APPARATUS FOR MAKING A DETERMINATION ABOUT AN EYE USING COLOR TEMPERATURE ADJUSTED AMBIENT LIGHTING

(71) Applicant: Ohio State Innovation Foundation, Columbus, OH (US)

(72) Inventor: Melissa Bailey, Gahanna, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 631 days.

This patent is subject to a terminal disclaimer.

(21) Appl. No.: 16/728,217

(22) Filed: Dec. 27, 2019

(65) Prior Publication Data
US 2021/0196118 A1    Jul. 1, 2021

(51) Int. Cl.
| | | |
|---|---|---|
| *A61B 3/02* | (2006.01) | |
| *A61B 3/10* | (2006.01) | |
| *A61B 3/113* | (2006.01) | |
| *A61B 3/12* | (2006.01) | |
| *A61B 3/024* | (2006.01) | |
| *A61B 3/103* | (2006.01) | |
| *G01J 5/60* | (2006.01) | |
| *A61B 3/15* | (2006.01) | |
| *A61B 3/14* | (2006.01) | |

(52) U.S. Cl.
CPC .............. *A61B 3/1035* (2013.01); *A61B 3/14* (2013.01); *A61B 3/158* (2013.01); *G01J 5/60* (2013.01)

(58) Field of Classification Search
CPC ......... A61B 3/02; A61B 3/102; A61B 3/1025; A61B 3/113; A61B 3/1015; A61B 3/1225; A61B 3/024
USPC ............... 351/246, 200, 205, 206, 209, 210, 351/221–223
See application file for complete search history.

(56) References Cited

U.S. PATENT DOCUMENTS

| | | |
|---|---|---|
| 4,293,198 A | 10/1981 | Kohayakawa |
| 5,180,907 A | 1/1993 | Udden et al. |
| 5,329,322 A | 7/1994 | Yancey |
| 5,632,282 A | 5/1997 | Hay et al. |

(Continued)

FOREIGN PATENT DOCUMENTS

| | | |
|---|---|---|
| CN | 104068827 | 10/2014 |
| CN | 110448267 | 11/2019 |

(Continued)

OTHER PUBLICATIONS

Office action issued for Japanese Patent Application No. 2020-187167, dated Mar. 22, 2022.

(Continued)

*Primary Examiner* — Dawayne Pinkney
(74) *Attorney, Agent, or Firm* — Meunier Carlin & Curfman LLC

(57) ABSTRACT

Disclosed herein are methods and apparatus for making a determination about an eye in ambient lighting conditions comprising detecting ambient light reflected out of an eye of a subject from a retina of the eye of the subject and making a determination about the eye of the subject based upon the reflected ambient light, wherein the ambient light is adjusted for color temperature when making the determination about the eye.

20 Claims, 9 Drawing Sheets

(56) References Cited

U.S. PATENT DOCUMENTS

| | | |
|---|---|---|
| 6,095,989 A | 8/2000 | Hay et al. |
| 6,409,342 B1 | 6/2002 | Ohnuma et al. |
| 6,419,638 B1 | 7/2002 | Hay et al. |
| 7,641,342 B2 | 1/2010 | Eberl et al. |
| 8,585,687 B2 | 11/2013 | Campbell |
| 8,591,027 B2 | 11/2013 | Su et al. |
| 8,619,405 B2 | 12/2013 | Van Heugten |
| 8,630,828 B2 | 1/2014 | Parker |
| 8,632,184 B2 | 1/2014 | Lai |
| 8,851,677 B2 | 10/2014 | Liebich |
| 10,219,687 B2 | 3/2019 | Wilkes |
| 10,986,991 B2 | 4/2021 | Bailey |
| 2003/0048929 A1 | 3/2003 | Golden et al. |
| 2003/0058405 A1 | 3/2003 | Cornsweet et al. |
| 2005/0057723 A1 | 3/2005 | Wakil et al. |
| 2006/0077581 A1 | 4/2006 | Schwiegerlin et al. |
| 2007/0076294 A1 | 4/2007 | Kitajima |
| 2010/0026957 A1 | 2/2010 | Tanguay, Jr. |
| 2011/0091084 A1 | 4/2011 | Li et al. |
| 2011/0279679 A1 | 11/2011 | Samuel et al. |
| 2013/0135181 A1 | 5/2013 | Eberl et al. |
| 2014/0111630 A1* | 4/2014 | R. Pires ............... A61B 3/113 348/78 |
| 2014/0160433 A1 | 6/2014 | Brown et al. |
| 2016/0019420 A1* | 1/2016 | Feng .................. G06V 40/40 382/117 |
| 2016/0128559 A1 | 5/2016 | Bailey |
| 2017/0118403 A1 | 4/2017 | Chu et al. |

FOREIGN PATENT DOCUMENTS

| | | |
|---|---|---|
| JP | H08-266471 | 10/1996 |
| JP | 2004-261212 A | 9/2004 |
| JP | 2011-110253 A | 6/2011 |
| JP | 2012-016606 | 1/2012 |
| JP | 2013-48376 A | 3/2013 |
| JP | 2014-151024 | 8/2014 |
| WO | WO2006/010611 | 2/2006 |
| WO | WO2007/069294 | 6/2007 |
| WO | WO2008/145786 | 12/2008 |
| WO | WO2011/100544 | 8/2011 |
| WO | WO2013/059663 | 4/2013 |
| WO | 2013/096473 A1 | 6/2013 |
| WO | 2014/175154 A1 | 10/2014 |

OTHER PUBLICATIONS

Office Action issued for Japanese Application No. 2017-524377, dated Apr. 20, 2020.

Blauensteiner, P., Wildenauer, H., Hanbury, A., & Kampel, M. (2006). On colour spaces for change detection and shadow suppression. Computer Vision Winter Workshop, Czech Pattern Recognition Society, Telc, Czech Republic, Feb. 6-8, 2006, 6 pages.

Chen, Ying-Ling, Bo Tan, and J. Lewis. "Simulation of eccentric photorefraction images." Optics express 11.14(2003): 1628-1642.

Cibis, Gerhard W. "Video vision development assessment (VVDA): combining the Brückner test with eccentric photorefraction for dynamic identification of amblyogenic factors in infants and children." Transactions of the American Ophthalmological Society 92 (1994): 643.

De la Cruz Cardona, Juan, José Ramón Jiménez, and Mª del Mar Pérez. "Colorimetric Analysis of Eccentric Photorefraction Techniques." Jul. 28, 2011. 4 pages.

R. Bruckner: "Exakte Strabismus Diagnostik bei 1/2-3jährigen Kindern mjt einem e'infachen Verfahren, dem <Durchleuchtungstest>", Ophthalmologica , vol. 144, No. Jan. 1, L962 (Jan. 1, 1962), pp. 184-198. (English translation not provided since listed as an "A" reference in the EESR. Applicant will obtain an English translation upon request.).

Hanbury, Allan. "A 3D-polar coordinate colour representation well adapted to image analysis." Image Analysis. Springer Berlin Heidelberg, 2003. 804-811.

Office Action and it's translation issued for Japanese Application No. 2017-524377, dated Aug. 5, 2019.

Extended European Search Report issued for European U.S. Appl. No. 15/856,408, dated Jul. 26, 2018.

International Search Report and Written Opinion of the International Searching Authority, Application No. PCT/US2015/059529, dated Mar. 11, 2016, 13 pages.

International Search Report and Written Opinion issued for Application No. PCT/US2019/068644, dated Feb. 27, 2020.

International Search Report and Written Opinion issued for Application No. PCT/US2019/068646, dated Mar. 3, 2020.

Office Action issued for Canadian Application No. 3,004,408, dated Nov. 5, 2021.

Office Action issued for Japanese Application No. 2020-187167, dated Aug. 10, 2021.

Notice of Allowance issued for U.S. Appl. No. 16/250,592, dated Feb. 4, 2021.

U.S. Patent and Trademark Office. Office Action issued in U.S. Appl. No. 16/728,220 dated Jul. 13, 2022. 31 pages.

U.S. Patent and Trademark Office Restriction Requirement issued in U.S. Appl. No. 16/728,220 dated Apr. 29, 2022. 6 pages.

U.S. Patent and Trademark Office. Office Action issued in U.S. Appl. No. 17/240,212 dated Aug. 17, 2022. 31 pages.

Final Office Action relating to U.S. Appl. No. 16/728,220, dated Nov. 28, 2022.

* cited by examiner

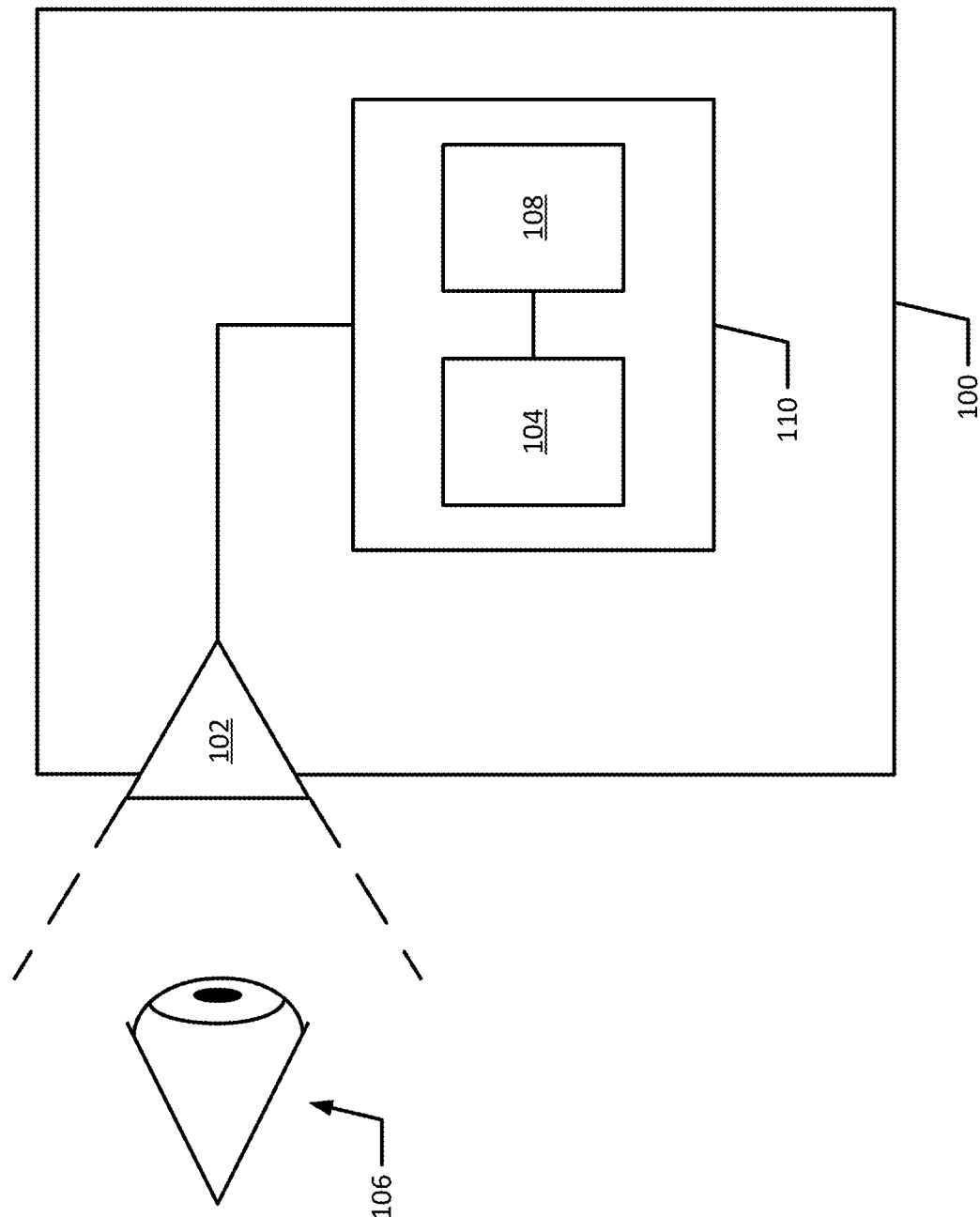

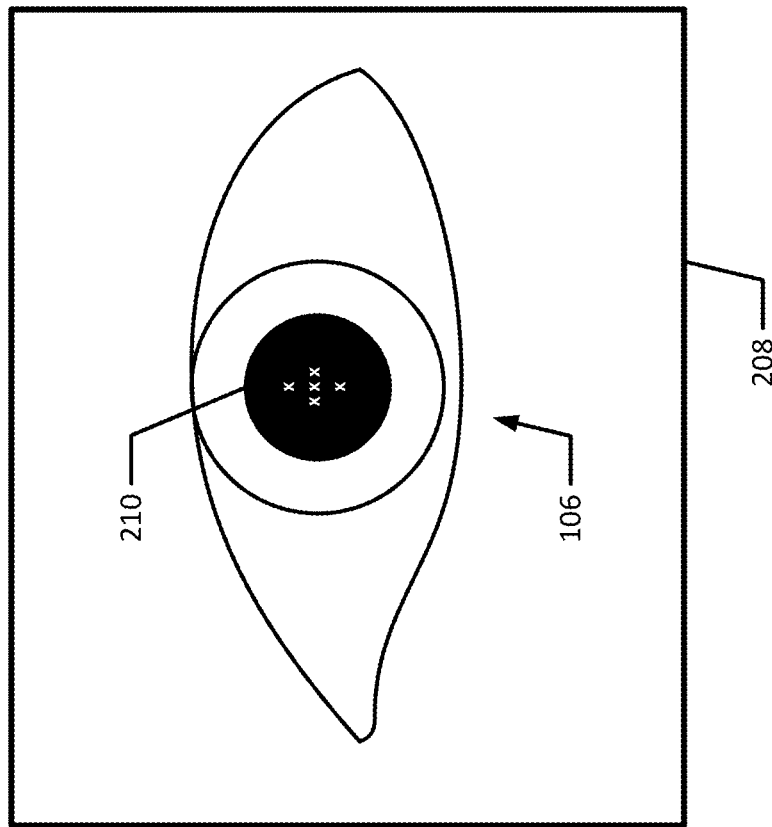
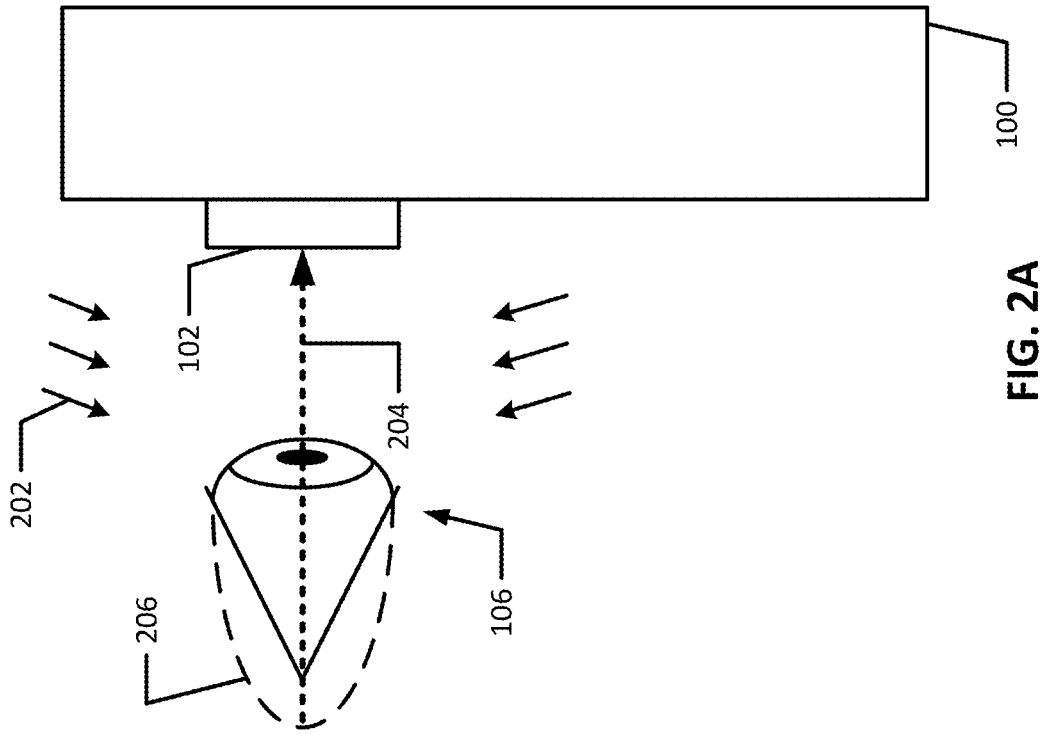

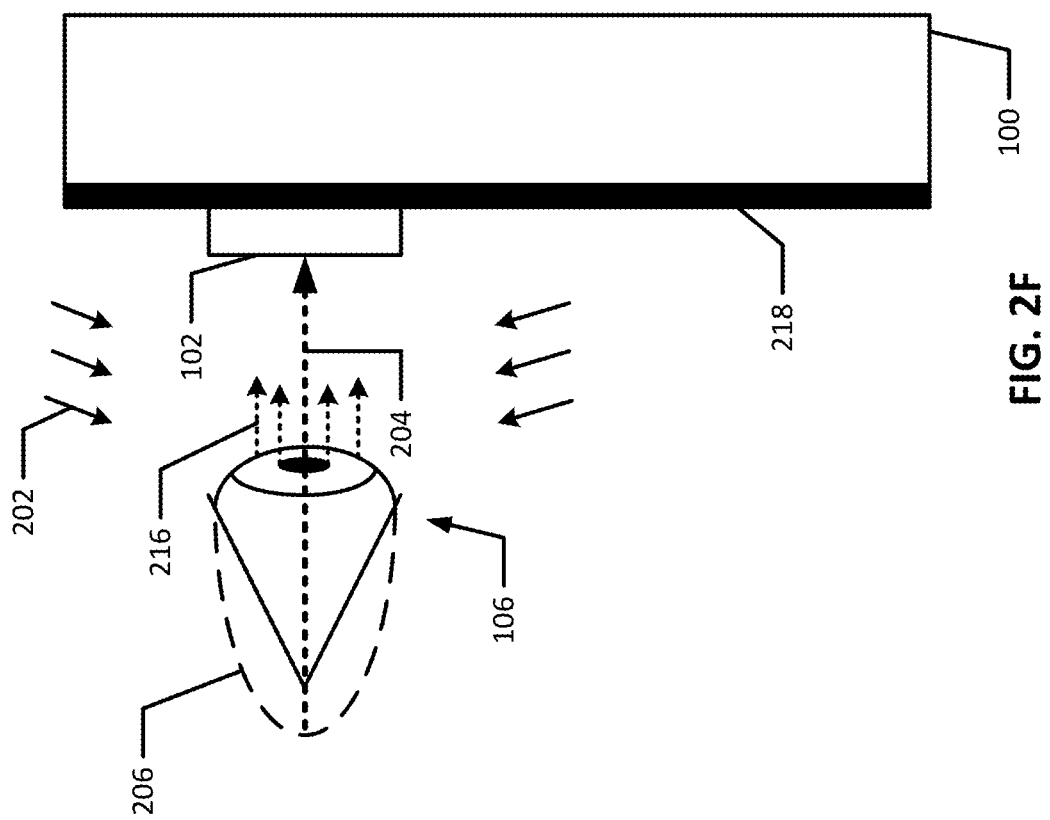

Determining A Color Temperature Of Ambient Light
402

Detecting Ambient Light Reflected Out Of An Eye Of A Subject From A Retina Of The Eye Of The Subject
404

Making A Determination About The Eye Of The Subject Based Upon The Reflected Ambient Light, Wherein The Reflected Ambient Light Is Adjusted Based On The Determined Color Temperature Of The Ambient Lighting;.
406

FIG. 4

Capturing An Image Of The Eye Of The Subject Using Only Ambient Lighting While Managing Non-Relevant Reflections
502

Determine An Average Red Intensity Of A Plurality Of Pixels Located Within At Least A Portion Of The Pupil Captured In The Image
504

Determine An Average Blue Intensity Of The Plurality Of Pixels Located Within At Least A Portion Of The Pupil Captured In The Image
506

Determine An Overall Intensity Of The Plurality Of Pixels Located Within At Least A Portion Of The Pupil Captured In The Image
508

Compare The Average Red Intensity And The Average Blue Intensity, Wherein The Comparison And The Determined Overall Intensity Are Used To Determine An Optical Quality Of The Eye.
510

FIG. 5

```
┌─────────────────────────────────────────────────┐
│  Determining A Color Temperature Of Ambient Lighting │
│                      602                         │
└─────────────────────────────────────────────────┘
                        │
┌─────────────────────────────────────────────────┐
│  Detected Reflected Ambient Light Out Of An Eye Of A │
│  Subject From A Retina Of The Eye Of The Subject │
│                      604                         │
└─────────────────────────────────────────────────┘
                        │
┌─────────────────────────────────────────────────┐
│  Detect An Overall Intensity Of Light From The Reflected │
│  Ambient Light From The Sensed Portion Of The Pupil Of │
│              The Eye Of The Subject              │
│                      606                         │
└─────────────────────────────────────────────────┘
                        │
┌─────────────────────────────────────────────────┐
│  Adjust The Overall Intensity Of Light Based On The │
│  Determined Color Temperature Of The Ambient Lighting │
│                      608                         │
└─────────────────────────────────────────────────┘
                        │
┌─────────────────────────────────────────────────┐     ┌──────────────────────┐
│  Determine A First Intensity Of A First Color From The │     │   A Determination    │
│  Reflected Ambient Light From The Sensed Portion Of The│     │  About The Eye Of    │
│        Pupil Of The Eye Of The Subject           │     │ The Subject Is Made  │
│                      610                         │     │   Based Upon The     │
└─────────────────────────────────────────────────┘     │  Reflected Ambient   │
                        │                                │  Light, Where The    │
┌─────────────────────────────────────────────────┐     │    Comparison And    │
│  Adjust The First Intensity Of Light Based On The │     │ Said Overall Intensity│
│  Determined Color Temperature Of The Ambient Lighting │     │  Are Used To Make    │
│                      612                         │     │  The Determination   │
└─────────────────────────────────────────────────┘     │  About The Eye Of    │
                        │                                │ The Subject Based    │
┌─────────────────────────────────────────────────┐     │ Upon The Reflected   │
│  Determine A Second Intensity Of A Second Color From The│     │   Ambient Light,     │
│  Reflected Ambient Light From The Sensed Portion Of The│     │ Adjusted For Color   │
│        Pupil Of The Eye Of The Subject           │     │     Temperature      │
│                      614                         │     │         620          │
└─────────────────────────────────────────────────┘     └──────────────────────┘
                        │                                           │
┌─────────────────────────────────────────────────┐                 │
│  Adjust The First Intensity Of Light Based On The │                 │
│  Determined Color Temperature Of The Ambient Lighting │                 │
│                      616                         │                 │
└─────────────────────────────────────────────────┘                 │
                        │                                           │
┌─────────────────────────────────────────────────┐                 │
│  A Relative Intensity Of The First Color And A Relative │─────────────┘
│   Intensity Of The Second Color Are Compared     │
│                      618                         │
└─────────────────────────────────────────────────┘
```

FIG. 6

METHODS AND APPARATUS FOR MAKING A DETERMINATION ABOUT AN EYE USING COLOR TEMPERATURE ADJUSTED AMBIENT LIGHTING

BACKGROUND

There are many existing devices that are used to detect the optical quality of the eye or other optical systems, including: autorefractors/ophthalmic refractometers, aberrometers, etc. All of the existing devices work by using a light source to illuminate the eye. Many devices, including the vast majority of autorefractors, use an infrared light source, but visible light sources are also used. Anyone who has used a standard camera with a flash will know that light from the flash will reflect off of the retina during photography. This reflected light will make the pupil appear red in a photograph of a human eye or appear greenish in a photograph of many animals' eyes. The reflected light will also have a particular pattern that is dependent upon the eye's optical distortions. Many existing/previous autorefractors or aberrometers are based on this principle, i.e., shining a light into the eye and then detecting the pattern of the reflected light after it has been distorted by the eye. The devices vary in the configuration or type of light source or in how the reflected light is detected (single images, lenslet arrays, telescope combined with a lenslet array, etc.). However, in each of those cases, a light is shined into the eye and then the magnitude of the refractive error is determined, and this is often based on the intensity slope of the light (brighter at either the top or the bottom of the pupil) that is reflected off of the retina and back out of the eye.

Therefore, methods, apparatus and systems are desired that improve the detection of an optical quality of the eye or other optical system and that overcome challenges in the art, some of which are described above.

SUMMARY

Described herein are devices and methods to measure optical distortions in the eye by monitoring the intensity of a first color of light versus intensity of a second color of light within the pupil of a subject under ambient lighting conditions, which is readily available light where no emitter of light is shined into the eye. For example, although there may be lamps and light fixtures in a room wherein devices and methods described in this disclosure are practiced, these sources or emitters of light are not used purposefully to illuminate the eye and the source of light is not directed into the eye. The subject can be a human or an animal. While the pupil may appear to be black or very dark in a photograph that does not use a flash, the pixel values do vary in magnitude based on the power of the eye. In the images that are obtained for embodiments of this invention, the information needed to measure the optical distortions of the eye is contained within the pixel values of the first and second color. In some instances, a color temperature is determined for the ambient lighting and lighting values such as intensity and/or overall brightness are adjusted for a color temperature of the ambient lighting.

Non-relevant reflections from the lens and corneal surface are blocked; else these reflections would otherwise obscure measurement of the light within the pupil. For example, the surface closest to the patient of the apparatus acquiring the images can be matte and black so that it does not create corneal reflections that would obscure the measurement, or a polarizing filter can be used.

Once this image is obtained, the pupil and its border are identified. Light within the pupil is then analyzed. No light is shined into the eye. The total intensity of the pupil is used in a formula that calculates the autorefraction result, and a minimum intensity is required, but differences in intensity across the pupil are not measured for autorefraction. The light in an eye with spherical refractive error does not have a slope; it is of uniform intensity within the pupil. Even the difference between the pixels of the first color and the second color is uniform across the pupil for spherical refractive error (i.e., no astigmatism). Ambient light from the room that is always reflecting off of the retina is measured. A difference in the intensity of the first color versus the second color pixel values is determined and compared; this difference is related to the eye's refractive error/glasses prescription. For example, the difference between the first color and second color pixels is a larger number in hyperopia (farsighted) and a lower number in myopia (nearsighted). Also, the light within the pupil of eyes with hyperopia is somewhat brighter than eyes with myopia. In the case of astigmatism, the intensity of individual pixels across the pupil will have a higher standard deviation than with hyperopia or myopia alone. In most eyes, the axis of the astigmatism is known to be regular, meaning that the two principal power meridians are 90 degrees apart. In the present disclosure, the presence of astigmatism within an optical system causes differences in intensity within the pupil. The more myopic meridian will be dimmer and the more hyperopic meridian will be brighter.

Disclosed herein is a method of making a determination about an eye. The method comprises determining, using a computing device, a color temperature of ambient lighting; detecting, using the computing device, ambient light reflected out of an eye of a subject from a retina of the eye of the subject; and making a determination about the eye of the subject based upon the reflected ambient light adjusted based on the determined color temperature. As described herein, the reflected light relies upon ambient light and no additional light emitter is required or directed toward the eye to create the reflected light. The determination about the eye is made based at least in part on an aspect of the reflected ambient light. For example, overall brightness and the intensity of one or more colors of the reflected ambient light, adjusted for color temperature, can be used to make the determination about the eye.

In one aspect, the determination made about the eye comprises the refractive error for the eye of the subject based at least in part on an aspect of the reflected ambient light.

Alternatively, or optionally, in reference to the above-described method, detecting, using the computing device, ambient light reflected out of an eye of a subject from a retina of the eye of the subject can further comprise capturing, using an image capture device, an image of the eye of a subject, wherein the image is captured using only ambient lighting conditions and wherein non-relevant reflections from the eye of the subject are managed while capturing the image; determining, using the computing device, an overall intensity of light from a plurality of pixels located within the at least a portion of a pupil captured in the image; determining, using the computing device, a first intensity of a first color from the plurality of pixels located within the at least a portion of a pupil of the eye of the subject captured in the image; determining, using the computing device, a second intensity of a second color from the plurality of pixels located within the at least a portion of the pupil of the eye of the subject captured in the image; and comparing, by the computing device, a relative intensity of the first color and a relative intensity of the second color, wherein the comparison and the overall intensity are used to make the determination about the eye of the subject based upon the reflected ambient light. Either the first or the second color can be any one or any combination of red green and blue.

In one aspect, the above described method can be used to make determinations about the eye that include an autorefraction or a photorefraction measurement. For example, capturing, using the image capture device, an image of the eye of the subject can comprise capturing a first image using only ambient lighting conditions with the image capture device through a spectacle lens or a contact lens while the subject is wearing the spectacle lens or the contact lens over the eye and capturing a second image using only ambient lighting conditions with the image capture device while the subject is not wearing the spectacle lens or the contact lens over the eye and the first image is compared to the second image and the determination about the eye of the subject based upon the reflected ambient is based on the comparison and comprises an estimated prescription for the spectacle lens or the contact lens.

Alternatively, or optionally, in reference to the above-described method, when the first intensity of the first color is brighter relative to the second intensity of the second color and the overall intensity is relatively brighter, the determination about the eye of the subject based upon the reflected ambient light comprises a positive value or hyperopia. Similarly, when the first intensity of the first color is dimmer relative to the second intensity of the second color and the overall intensity is relatively dimmer, the determination about the eye of the subject based upon the reflected ambient light comprises a negative value or myopia.

The above-described method can also be used to make a determination about the eye such as astigmatism. For example, the method can further comprise making a first determination about the eye of the subject based upon the reflected ambient light from a first plurality of pixels located within the at least a portion of the pupil of the eye of the subject captured in the image; making a second determination from a second plurality of pixels located within the at least a portion of the pupil of the eye of the subject captured in the image, wherein the second plurality of pixels are a subset of the first plurality of pixels; making a third determination from a third plurality of pixels located within the at least a portion of the pupil of the eye of the subject captured in the image, wherein the third plurality of pixels are a subset of the first plurality of pixels and are separate from the second plurality of pixels; and comparing the first determination, the second determination and the third determination to make the determination about the eye of the subject based upon the reflected ambient light. Comparing the first determination, the second determination and the third determination to make the determination about the eye of the subject based upon the reflected ambient light can comprise one or more of determining a standard deviation of the first determination to the second determination, a standard deviation of the first determination to the second determination, or a standard deviation of the second determination to the third determination, wherein the determined standard deviation indicates the determination about the eye of the subject based upon the reflected ambient light. As noted above, the determination about the eye of the subject based upon the reflected ambient light can be a presence or an absence of astigmatism. Further, when the presence of astigmatism is detected, an amount of astigmatism can be determined by comparing the overall intensity and the relative intensity of the first color or the relative intensity of the second color of various regions of the pupil.

As noted above, the method comprises managing non-relevant reflections from the eye while capturing the image. Generally, this comprises managing reflections from a cornea or a lens of the eye of the subject while capturing the image. For example, managing non-relevant reflections from the eye while capturing the image can comprise placing a polarizing filter over a lens of the image capture device or between the image capture device and the eye of the subject. Alternative or optionally, managing non-relevant reflections from the eye while capturing the image can comprise blocking light that would lead to reflections from a corneal surface of the eye or a lens of the eye. For example, managing non-relevant reflections from the eye while capturing the image can comprise providing a surface that absorbs light or prevents the non-relevant reflections from the eye while capturing the image. The surface can have a black matte finish. In one aspect, the surface can comprise a portion of the image capture device. For example, the surface can comprise at least a portion of a case that houses the image capture device.

In reference to the above-described method, the image capture device can comprise a smart phone or other mobile computing device having a camera. Generally, the image capture device can capture a still image or a video of the eye of the subject.

The above-described method can be used to make a determination about the eye of a person having a smaller than average pupil. For example, where the subject's pupil has a diameter of approximately 2 mm or less. Further, the subject's pupil can be a natural pupil or an artificial pupil. The eye of the subject can be the subject's left eye or right eye, or the subject's left eye and right eye. In one aspect, the method can further comprise detecting an intensity for the ambient light conditions and providing an indication if the ambient light conditions are too low for the image capture device to capture the image of the eye of the subject.

Also disclosed herein is an alternate method of making a determination about an eye. The method comprises determining a color temperature of ambient lighting; capturing, using an image capture device, an image of an eye of a subject, wherein the image is captured using only ambient lighting conditions and wherein non-relevant reflections from a cornea and a lens of the eye of the subject are managed while capturing the image; determining, using a computing device, an overall intensity of light, adjusted for color temperature, from a plurality of pixels located within at least a portion of a pupil captured in the image, wherein the plurality of pixels comprise red, green and blue pixels; determining, using the computing device, an average red intensity, adjusted for color temperature, from the plurality of pixels located within the at least a portion of the pupil captured in the image; determining, using the computing device, an average blue intensity, adjusted for color temperature, from the plurality of pixels located within the at least a portion of a pupil captured in the image; and determining, by the computing device, using the average red intensity, the average blue intensity and the determined overall intensity an optical quality of the eye.

Similarly as described above, the determined optical quality of the eye can comprise an autorefraction or photorefraction measurement such that the method can be used to provide an estimated prescription for spectacle lens or contact lens. Further, the method can be used to determine an optical quality of the eye such as a positive value or hyperopia, a negative value or myopia, the presence or absence of astigmatism, and an amount of astigmatism if is found to be present.

Another aspect of the disclosure is an apparatus for performing the above-described methods. In one embodiment, the apparatus comprises a sensor. In one aspect the sensor may comprise an image capture device; a memory; and a processor in communication with the memory and the image capture device, wherein the processor executes computer-readable instructions stored in the memory that cause the processor to: determine a color temperature of ambient light; capture, using the image capture device, an image of an eye of a subject, wherein the image is captured using only ambient lighting conditions and wherein non-relevant reflections from the eye of the subject are managed while capturing the image; detect, from the image of the eye of the subject, ambient light reflected out of the eye of a subject from a retina of the eye of the subject; and make a determination about the eye of the subject based upon the detected reflected ambient light, adjusted for color temperature.

In one aspect, the determination made about the eye by the apparatus comprises the refractive error for the eye of the subject based at least in part on an aspect of the reflected ambient light.

Alternatively, or optionally, the apparatus can be used for detecting ambient light reflected out of an eye of a subject from a retina of the eye of the subject by determining an overall intensity of light, adjusted for color temperature, from a plurality of pixels located within the at least a portion of a pupil captured in the image; determining a first intensity of a first color, adjusted for color temperature, from the plurality of pixels located within the at least a portion of a pupil of the eye of the subject captured in the image; determining a second intensity of a second color, adjusted for color temperature, from the plurality of pixels located within the at least a portion of the pupil of the eye of the subject captured in the image; and comparing a relative intensity of the first color and a relative intensity of the second color, wherein the comparison and the overall intensity are used to make the determination about the eye of the subject based upon the reflected ambient light. Either the first or the second color can be any one or any combination of red green and blue.

In one aspect, the above described apparatus can make determinations about the eye that include an autorefraction or a photorefraction measurement. For example, when capturing, using the image capture device, an image of the eye of the subject the processor can execute computer-readable instructions store in the memory to capture a first image using only ambient lighting conditions with the image capture device through a spectacle lens or a contact lens while the subject is wearing the spectacle lens or the contact lens over the eye and capture a second image using only ambient lighting conditions with the image capture device while the subject is not wearing the spectacle lens or the contact lens over the eye and the first image is compared to the second image and the determination about the eye of the subject based upon the reflected ambient is based on the comparison and comprises an estimated prescription for the spectacle lens or the contact lens.

Alternatively, or optionally, the processor of the apparatus can execute computer-readable instructions such that when the first intensity of the first color is brighter relative to the second intensity of the second color and the overall intensity is relatively brighter, the determination about the eye of the subject based upon the reflected ambient light comprises a positive value or hyperopia. Similarly, when the first intensity of the first color is dimmer relative to the second intensity of the second color and the overall intensity is relatively dimmer, the determination about the eye of the subject based upon the reflected ambient light comprises a negative value or myopia.

The above-described apparatus can also be used to make a determination about the eye such as astigmatism. For example, the processor of the apparatus can execute computer-readable instructions for making a first determination about the eye of the subject based upon the reflected ambient light from a first plurality of pixels located within the at least a portion of the pupil of the eye of the subject captured in the image; making a second determination from a second plurality of pixels located within the at least a portion of the pupil of the eye of the subject captured in the image, wherein the second plurality of pixels are a subset of the first plurality of pixels; making a third determination from a third plurality of pixels located within the at least a portion of the pupil of the eye of the subject captured in the image, wherein the third plurality of pixels are a subset of the first plurality of pixels and are separate from the second plurality of pixels; and comparing the first determination, the second determination and the third determination to make the determination about the eye of the subject based upon the reflected ambient light. Comparing the first determination, the second determination and the third determination to make the determination about the eye of the subject based upon the reflected ambient light can comprise one or more of determining a standard deviation of the first determination to the second determination, a standard deviation of the first determination to the second determination, or a standard deviation of the second determination to the third determination, wherein the determined standard deviation indicates the determination about the eye of the subject based upon the reflected ambient light. As noted above, the determination about the eye of the subject based upon the reflected ambient light can be a presence or an absence of astigmatism. Further, when the presence of astigmatism is detected, an amount of astigmatism can be determined by comparing the overall intensity and the relative intensity of the first color or the relative intensity of the second color of various regions of the pupil.

As noted above, the apparatus can manage non-relevant reflections from the eye while capturing the image. Generally, this comprises managing reflections from a cornea or a lens of the eye of the subject while capturing the image. For example, managing non-relevant reflections from the eye while capturing the image can comprise placing a polarizing filter over a lens of the image capture device or between the image capture device and the eye of the subject. Alternative or optionally, managing non-relevant reflections from the eye while capturing the image can comprise blocking light that would lead to reflections from a corneal surface of the eye or a lens of the eye. For example, managing non-relevant reflections from the eye while capturing the image can comprise providing a surface that absorbs light or prevents the non-relevant reflections from the eye while capturing the image. The surface can have a black matte finish. In one aspect, the surface can comprise a portion of the image capture device. For example, the surface can comprise at least a portion of a case that houses the image capture device.

In reference to the above apparatus, the image capture device can comprise a smart phone or other mobile computing device having a camera. Generally, the image capture device can capture a still image or a video of the eye of the subject.

The above-described apparatus can be used to make a determination about the eye of a person having a smaller than average pupil. For example, where the subject's pupil has a diameter of approximately 2 mm or less. Further, the subject's pupil can be a natural pupil or an artificial pupil. The eye of the subject can be the subject's left eye or right eye, or the subject's left eye and right eye. In one aspect, the apparatus can further comprise a light meter to detect an intensity for the ambient light conditions and provide an indication if the ambient light conditions are too low for the image capture device to capture the image of the eye of the subject.

Further described and disclosed herein is a method of making a determination about an eye of a subject based upon ambient light reflected out of the eye. The method comprises determining, using a computing device, a color temperature of ambient lighting. In some instances, determining the color temperature of ambient lighting comprises determining, by the computing device, the color temperature of the ambient lighting using the sclera and/or pupil of the eye of the subject, wherein reflected light of the sclera and/or pupil of the eye is sensed by the sensor. In some instances, determining the color temperature of the ambient lighting using the sclera and/or pupil of the eye of the subject comprises using reflected light from the sclera and/or pupil of the eye to sense the color temperature of the ambient lighting. In some instances, determining the color temperature of the ambient lighting using the sclera and/or pupil of the eye of the subject comprises acquiring, in real-time, reflected light from the sclera and/or pupil of the eye that are used by the computing device to sense the color temperature of the ambient lighting. In some instances, the color temperature of the ambient lighting using the sclera and/or pupil of the eye of the subject comprises determining, by the computing device, a hue and/or luminance of the sclera of the eye of the subject and the computing device using the hue and/or luminescence to determine the color temperature of the ambient lighting. In some instances, determining the color temperature of ambient lighting comprises determining, by the computing device, the color temperature of the ambient lighting using an external white balance card wherein reflected light from the white balance card is sensed by the sensor.

The method further comprises detecting reflected ambient light out of an eye of a subject from a retina of the eye of the subject. In one aspect the detecting comprises sensing, using a sensor, at least a portion of the eye of the subject, wherein the sensing is performed using only ambient lighting conditions and wherein non-relevant reflections from the eye of the subject are managed while sensing the portion of the eye, and wherein the sensed portion of the eye comprises at least a portion of a pupil of the eye of the subject. In some instances, sensing, using the sensor, the portion of the eye of the subject comprises sensing at a first time through a spectacle lens or a contact lens while the subject is wearing the spectacle lens or the contact lens over the eye and sensing at a second time while the subject is not wearing the spectacle lens or the contact lens over the eye and the first sensing information is compared to the second sensing information and the determination about the eye of the subject based upon the reflected ambient light is based on the comparison and comprises an estimated prescription for the spectacle lens or the contact lens. In some instances, managing non-relevant reflections from the eye while capturing the image comprises managing reflections from a cornea or a lens of the eye of the subject while sensing the eye. In other instances, managing non-relevant reflections from the eye while sensing the eye comprises placing a polarizing filter over a lens of the sensor or between the sensor and the eye of the subject, or wherein managing non-relevant reflections from the eye while sensing the eye comprises blocking light that would lead to reflections from a corneal surface of the eye or a lens of the eye, or wherein managing non-relevant reflections from the eye while sensing the eye comprises providing a surface that absorbs light or prevents the non-relevant reflections from the eye while sensing the eye.

The method further comprises determining an overall intensity of light from the reflected ambient light from the sensed portion of the pupil of the eye of the subject. The overall intensity of light is adjusted by the computing device based on the determined color temperature of the ambient lighting. A first intensity of a first color from the reflected ambient light from the sensed portion of the pupil of the eye of the subject is determined. The first intensity of the first color is adjusted by the computing device based on the determined color temperature of the ambient lighting. A second intensity of a second color from the reflected ambient light from the sensed portion of the pupil of the eye of the subject is determined. In some instances, the first color comprises any one or any combination of red, green, and blue and the second color comprises any one or any combination of red, green, and blue. The second intensity of the second color is adjusted by the computing device based on the determined color temperature of the ambient lighting. A relative intensity of the first color and a relative intensity of the second color are compared, and a determination about the eye of the subject is made based upon the reflected ambient light, where the comparison and the overall intensity are used to make the determination about the eye of the subject based upon the reflected ambient light, adjusted for color temperature.

In some instances, the first intensity of the first color is brighter relative to the second intensity of the second color and the overall intensity is relatively brighter in luminescence than a myopic eye, and the determination about the eye of the subject based upon the reflected ambient light comprises a positive value or hyperopia.

In some instances, the first intensity of the first color is dimmer relative to the second intensity of the second color and the overall intensity is relatively dimmer in luminescence than a myopic eye, and the determination about the eye of the subject based upon the reflected ambient light comprises a negative value or myopia.

In some instances, the determination about the eye of the subject based upon the reflected ambient light comprises an autorefraction or a photorefraction measurement.

In some instances, the method may further comprise making a first determination about the eye of the subject based upon the reflected ambient light from a first portion of the sensed pupil of the eye; making a second determination from a second portion of the sensed pupil of the eye of the subject, wherein the second portion of the sensed pupil is a subset of the first portion of the sensed pupil of the eye; making a third determination from a third portion of the sensed pupil of the eye of the subject, wherein the third portion of the pupil is a subset of the first portion of the sensed pupil of the eye and is separate from the second sensed portion of the eye; comparing the first determination, the second determination and the third determination to make the determination about the eye of the subject based upon the reflected ambient light. In some instances, comparing the first determination, the second determination and the third determination to make the determination about the eye of the subject based upon the reflected ambient light comprises one or more of determining a standard deviation of the first determination to the second determination, a standard deviation of the first determination to the third determination, or a standard deviation of the second determination to the third determination, wherein the determined standard deviation indicates the determination about the eye of the subject based upon the reflected ambient light. In some instances, the determination about the eye of the subject based upon the reflected ambient light is a presence or an absence of astigmatism. In some instances, the presence of astigmatism is detected and an amount of astigmatism is determined by comparing the overall intensity and the relative intensity of the first color or the relative intensity of the second color of various regions of the pupil.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1 illustrates an exemplary overview apparatus for making a determination about the eye of a subject in ambient lighting conditions;

FIG. 2A illustrates an example of an apparatus for capturing an image of the eye and making a determination about an eye in ambient lighting conditions;

FIG. 2B illustrates an image of the eye captured by an apparatus for capturing an image of the eye and making a determination about an eye in ambient lighting conditions;

FIG. 2F illustrates an example of an apparatus for capturing an image of the eye using a surface and making a determination about an eye in ambient lighting conditions;

FIG. 4 illustrates an example method for making a determination about an eye of a subject based upon ambient light reflected out of the eye;

FIG. 5 illustrates an alternate example method for making a determination about an eye of a subject based upon ambient light reflected out of the eye; and FIG. 6 is a flowchart illustrating a method of making a determination about an eye of a subject based upon ambient light reflected out of the eye.

DETAILED DESCRIPTION

Figure 2E:
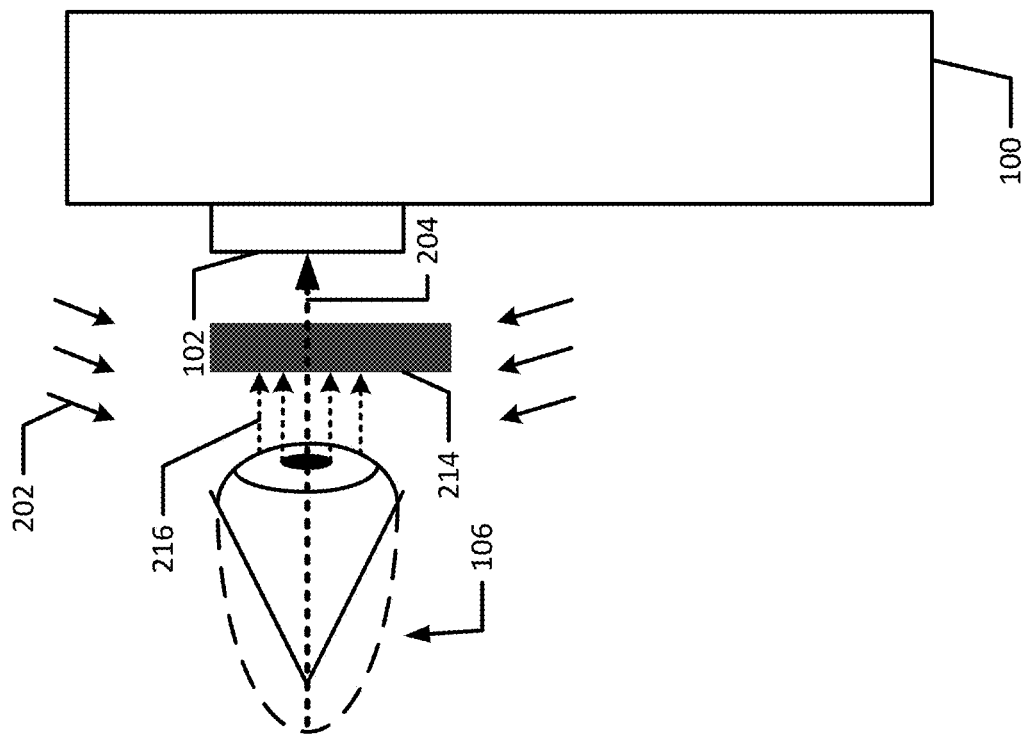
FIG. 2E illustrates an example of an apparatus for capturing an image of the eye using polarizing filters and making a determination about an eye in ambient lighting conditions.

Unless defined otherwise, all technical and scientific terms used herein have the same meaning as commonly understood by one of ordinary skill in the art. Methods and materials similar or equivalent to those described herein can be used in the practice or testing of the present disclosure.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

FIG. 1 illustrates an exemplary overview apparatus for making a determination about the eye of a subject in ambient lighting conditions. As shown in FIG. 1, one embodiment of the apparatus 100 comprises a sensor 102. In some instances sensor 102 may be an image capture mechanism In some aspects, the image capture mechanism can be a camera that can capture still and/or video images. For example, the image capture mechanism may be a digital camera, but can be an analog device equipped with or in communication with an appropriate analog/digital converter. The image capture mechanism may also be a webcam, scanner, recorder, or any other device capable of capturing a still image or a video. In other instances, the sensor 102 may be one or more sensing mechanisms that sense light in the visible and/or invisible (e.g., infrared and ultraviolet) spectrums.

In one aspect, the sensor 102 is in direct communication with a computing device 110 through, for example, a network (wired (including fiber optic), wireless or a combination of wired and wireless) or a direct-connect cable (e.g., using a universal serial bus (USB) connection, IEEE 1394 "Firewire" connections, and the like). In other aspects, the sensor 102 can be located remotely from the computing device 110, but capable of capturing an image and storing it on a memory device such that the image can be downloaded or transferred to the computing device 110 using, for example, a portable memory device and the like. In one aspect, the computing device 110 and the sensor 102 can comprise or be a part of a device such as a smart phone, table, laptop computer or any other mobile computing device.

In a basic configuration, the computing device 110 can be comprised of a processor 104 and a memory 108. The processor 104 can execute computer-readable instructions that are stored in the memory 108. Moreover, images captured by the sensor 102, whether still images or video, can be stored in the memory 108 and processed by the processor 104 using computer-readable instructions stored in the memory 108.

The processor 104 is in communication with the sensor 102 and the memory 108. The processor 104 can execute computer-readable instructions stored on the memory 108 to capture, using the sensor 102, an image of an eye 106 of a subject, or an image of part of the eye of the subject, or an image of an image of the eye that is formed by the cornea and/or crystalline lens of the subject. No light source, other than ambient lighting, is required to capture the image. The image is captured using only ambient lighting conditions and does not require an additional light source to be directed into the eye 106. While capturing the image of the eye 106, non-relevant reflections from the eye 106 of the subject are managed.

The processor 104 can further execute computer-readable instructions stored on the memory 108 to detect ambient light reflected out of the eye 106 of the subject from the retina of the eye 106 of the subject and to make a determination about the eye 106 of the subject based upon the detected reflected ambient light. In some instances, ambient light reflected out of the eye 106 of the subject from the retina of the eye 106 of the subject and the determination about the eye 106 of the subject based upon the detected reflected ambient light is detected from the image of the eye 106 of the subject. Generally, the processor 104 of the apparatus 100 executing computer-readable instructions stored in the memory 108 that cause the processor 104 to make a determination about the eye 106 of the subject based at least in part on an aspect of the reflected ambient light. Such aspects can include, for example, an overall brightness or intensity of the reflected ambient light as determined in a plurality of pixels of the image acquired by the sensor 102 or as determined based on reflected ambient light using the sensor 102. The aspects can also include one or more colors, or wavelengths, or region of visible the visible light spectrum of the reflected ambient light also as determined from the plurality of pixels of the image acquired by the sensor 102 or as determined based on reflected ambient light using the sensor 102. For example, the processor 104 executing computer-readable instructions stored in the memory 108 can cause the processor 104 to make a determination about the eye 106 based at least in part on the overall brightness or intensity of the red, green and blue pixels that comprise the reflected ambient light as determined from the image acquired by the sensor 102. Overall brightness can be determined, as a non-limiting example, using methods and software developed by Allan Hanbury (see, for example, "A 3D-Polar Coordinate Colour Representation Well Adapted to Image Analysis," Hanbury, Allan; Vienna University of Technology, Vienna, Austria, 2003), which is fully incorporated herein by reference and made a part hereof. The processor 104 also uses the relative intensity of red, green or blue found in the plurality of pixels of the image acquired by the sensor 102 or as determined based on reflected ambient light using the sensor 102 to make the determination about the eye 106. For example, using at least in part an aspect of the reflected ambient light as determined from an image of the eye 106 as captured by the sensor 102, the processor 104 executing computer-readable instructions stored in the memory 108 can make determinations about the eye 106 comprising a refractive error for the eye 106 of the subject. In other words, using at least in part an overall brightness or intensity of the reflected ambient light as determined in a plurality of the pixels of the image acquired by the sensor 102 or as determined based on reflected ambient light using the sensor 102 and the relative intensity of one or more colors of the reflected ambient light also as determined from the plurality of pixels of the image acquired by the sensor 102 or as determined based on reflected ambient light using the sensor 102, the processor 104 executing computer-readable instructions stored in the memory 108 can make determinations about the eye 106 including a refractive error for the eye 106 of the subject. In other instances, the processor 104 executing computer-readable instructions stored in the memory 108 can be used with the sensor 102 to assess the ambient light reflected within the pupil, or image of the pupil, and determine a hue and/or luminance of the reflected light within the pupil of the eye 106 of the subject and then the determined hue and/or luminance of the reflected ambient light within the pupil, or image of the pupil, can be used by the processor 104 executing computer-readable instructions stored in the memory 108 to make determinations about the eye 106 including a refractive error for the eye 106 of the subject.

As shown in FIG. 2A, in some instances the sensor 102 of the apparatus 100 captures an image (FIG. 2B) 208 of the eye 106. The processor 104 of the apparatus 100 can execute computer-readable instructions stored in the memory 108 that cause the processor 104 to detect, from the image 208 of the eye, ambient light 202 reflected 204 out of an eye 106 of the subject from the retina 206 of the eye 106 of the subject and determine the overall intensity of the plurality of pixels (example pixels are shown in FIG. 2B as white "x" in the pupil 210 of the image 208 of the eye) within the pupil 210 or a portion of the pupil 210; determine an intensity of a first color from a the plurality of pixels located within the pupil 210 or at least a portion of a pupil 210 of the eye of the subject captured in the image 208; determine an intensity of a second color from the plurality of pixels located within the pupil 201 or at least a portion of the pupil 210 of the eye of the subject captured in the image 208; and calculate refractive error or glasses prescription based on regression analysis. The regression analysis includes at least one of the following elements (1) the overall intensity or brightness of the pixels within pupil 210 or a portion of the pupil 210; and (2) the relative intensity of a first color from a first one or more pixels located within at least a portion of a pupil 210 of the eye of the subject captured in image 208 as compared to a second color from a second one or more pixels located within the at least a portion of the pupil 210 of the eye of the subject captured in image 208. Optionally, the regression analysis can also include (3) the color of the iris of the subject captures in image 208; and (4) the overall intensity of the ambient lighting at the time the image is captured with the sensor 102. For example, when the intensity of the first color is brighter relative to the intensity of the second color and the overall intensity is relatively brighter, the determination about the eye of the subject based upon the reflected ambient light can comprise a positive value or hyperopia. Alternatively, when the intensity of the first color is dimmer relative to the intensity of the second color and the overall intensity is relatively dimmer, the determination about the eye of the subject based upon the reflected ambient light can comprise a negative value or myopia.

For example, the first color can comprise any one or any combination of red, green, and blue and the second color can comprise any one or combination of red, green, and blue that is not used as the first color.

Figure 2C:
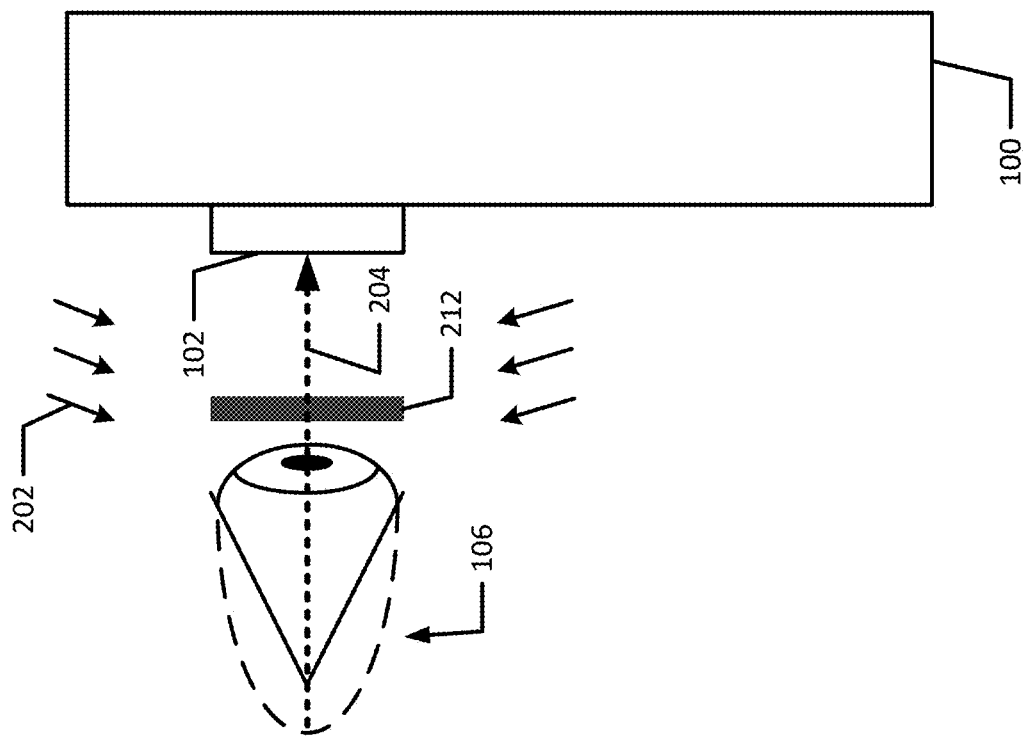
FIG. 2C illustrates an example of an apparatus for capturing an image of the eye and making a determination about an eye in ambient lighting conditions.

By performing the steps described above, the processor 104 of the apparatus 100 can execute computer-readable instructions stored in the memory 108 that cause the processor 104 to make an autorefraction or a photorefraction measurement. For example, as shown in FIG. 2C, the apparatus 100 can capture, using the sensor 102, an image 208 of the eye 106 of the subject using only ambient lighting 202 conditions through a spectacle lens or a contact lens (both shown as 212 in FIG. 2C) while the subject is wearing the spectacle lens or the contact lens 212 over the eye 106. The image capturing device 102 of the apparatus 100 then captures a second image using only ambient lighting 202 conditions while the subject is not wearing the spectacle lens or the contact lens 212 over the eye (see, for example, FIG. 2A) and the processor 104 executes computer-readable instructions stored in the memory 108 that cause the processor 104 to compare the first image to the second image and the determination about the eye of the subject based upon the reflected 204 ambient light is based on the comparison and comprises an estimated prescription for the spectacle lens or the contact lens 212.

Figure 2D:
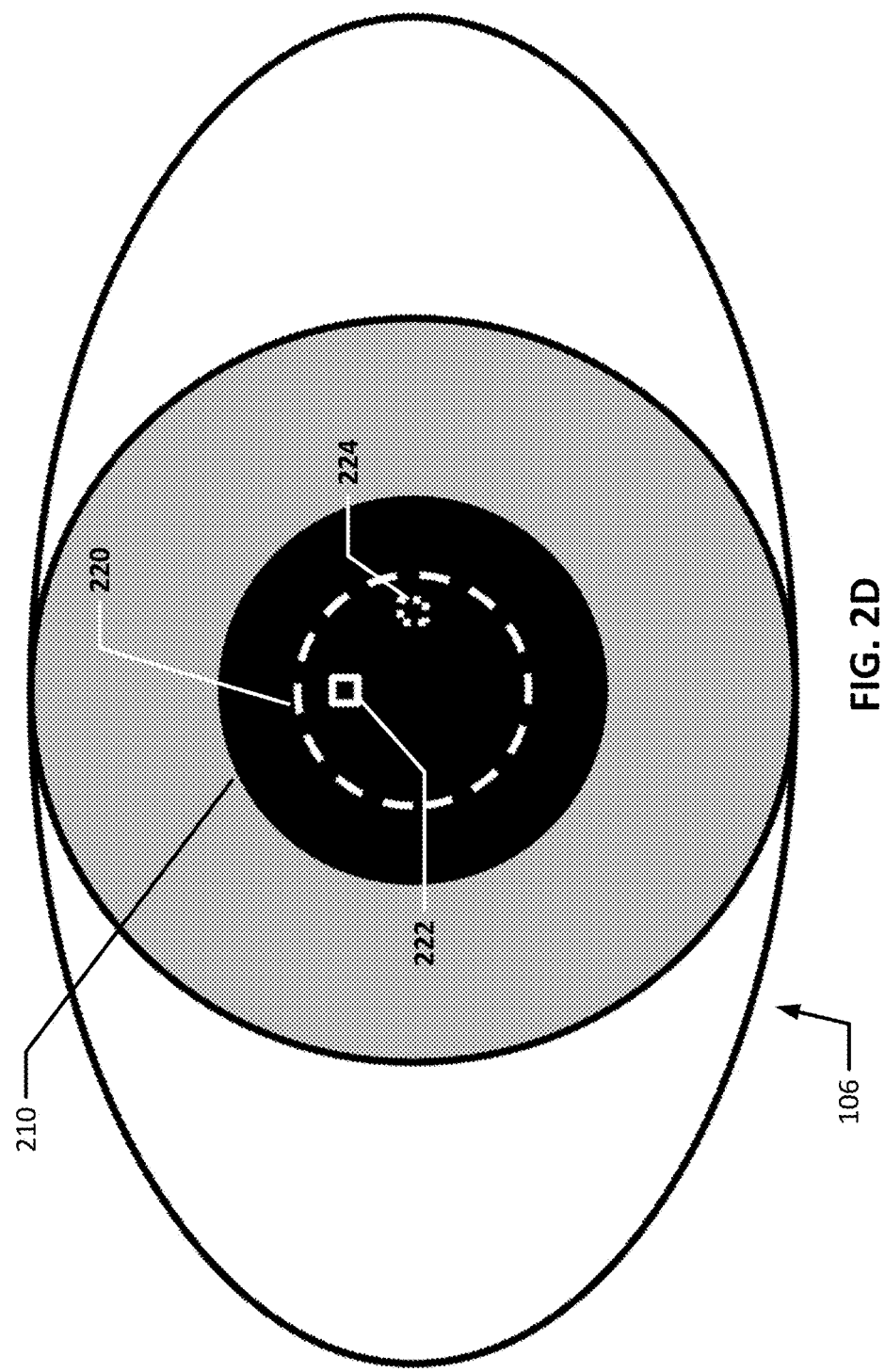
FIG. 2D illustrates an image of an eye that can be used to make a determination about the eye such as astigmatism.

Referring now to FIG. 2D, in yet another aspect, the processor 104 can execute computer-readable instructions stored in the memory 108 that cause the processor 104 to make a first determination about the eye 106 of the subject based upon the reflected ambient light from a first plurality of pixels 220 located within the at least a portion of the pupil 210 of the eye 106 of the subject captured in the image 208; make a second determination from a second plurality of pixels 222 located within the at least a portion of the pupil 210 of the eye 106 of the subject captured in the image 208, wherein the second plurality of pixels 222 are a subset of the first plurality of pixels 210; make a third determination from a third plurality of pixels 224 located within the at least a portion of the pupil 210 of the eye 106 of the subject captured in the image 208, wherein the third plurality of pixels 224 are a subset of the first plurality of pixels 210 and are separate from the second plurality of pixels 222; and compare the first determination, the second determination and the third determination to make the determination about the eye 106 of the subject based upon the reflected ambient light. For example, comparing the first determination, the second determination and the third determination to make the determination about the eye 106 of the subject based upon the reflected ambient light can comprise one or more of determining a standard deviation of the first determination to the second determination, a standard deviation of the first determination to the third determination, or a standard deviation of the second determination to the third determination, wherein the determined standard deviation indicates the determination about the eye 106 of the subject based upon the reflected ambient light. The determination made about the eye 106 of the subject based upon the reflected ambient light can be the presence or absence of astigmatism. The amount of astigmatism, once detected, can be determined by comparing the overall intensity and the relative intensity of the first color or the relative intensity of the second color of various regions of the pupil. For example, measuring one or more of hyperopia or myopia at the various regions of the pupil using the apparatus 100, as described herein, can be used to determine the amount of astigmatism present in the eye 106.

Consider the following example, again referring to FIG. 2D. If a determination of the eyes using the methods and apparatus described herein on the central region of the pupil (entire white dashed circle) 220 for someone with myopia (Ex: −2.00) and no astigmatism, a value of −2.00 would also be obtained in the sub-regions at 90 degrees (solid square) 222 and 0 degrees (dashed square) 224. If someone has astigmatism, a refractive error of −2.00 may be obtained if the whole pupil central region of the pupil (entire white dashed circle) 210 is analyzed using the methods and apparatus described herein, but if the sub-region at 90 degrees (solid square) 222 is analyzed and determined to have a refractive error of −1.00 and the sub-region at 0 degrees (dashed square) 224 is analyzed and determined to have a refractive error of −3.00, the standard deviation would be higher in the case of astigmatism where the sub-regions 222, 224 would be −1.00 and −3.00, respectively. Thus, a prescription for corrective lenses also needs to be −1.00 and −3.00 in those two sub-regions 222, 224, rather than an overall −2.00 for the central pupil region 220. These numbers are also just examples. They could be positive, negative, or both (one of each). Also, many sub-regions can be evaluated to make a determination about the eye. In this example the two sub-regions are at 90 degrees and 0 degrees, but they could be at any location throughout the pupil 210.

As described herein, the apparatus 100 or the sensor 102 can manage non-relevant reflections from a cornea and a lens of the eye 106 of the subject while capturing the image 208. Such non-relevant reflections can affect the determination about the eye of the subject based upon the reflected ambient light. Managing the non-relevant reflections can include, for example and as shown in FIG. 2E, the use of a polarizing filter 214, wherein non-relevant reflections 216 from the eye 106 are managed while capturing the image 208 by placing the polarizing filter 214 over a lens of the sensor 102 or between the sensor 102 and the eye 106 of the subject when capturing the image 208.

In yet another aspect, as shown in FIG. 2F, the apparatus 100 can further comprise a surface 218, wherein non-relevant reflections 216 from the eye 106 are managed while capturing the image 208 comprise the surface 218 absorbing light or preventing the non-relevant reflections 216 from the eye 106 while capturing the image 208. For example, when acquiring the image 208 the apparatus 100 including the sensor 102 can be placed close to the eye 106 such that non-relevant reflections 216 are minimized and those that do occur are absorbed or prevented by the surface 218. For example, the apparatus 100 including the sensor 102 can be placed from approximately 4 to 10 cm away from the eye 106 while capturing the image 208, or the apparatus 100 including the sensor 102 can be placed from approximately 8 to 9 cm away from the eye 106 while capturing the image 208. The surface 218 can comprise, for example, a surface having a black matte finish to facilitate the absorption of ambient light and prevent of non-relevant reflections. The surface 218 can comprise a portion of the sensor 102 or the apparatus 100, including a case that may house at least a portion of the sensor 102 or the apparatus 100. For example, the sensor 102 may comprise at least a portion of a smart phone or other mobile computing device having a camera and the surface 218 can be at least a portion of a case that houses the smart phone or other mobile computing device having a camera.

This disclosure contemplates apparatus that can be used make determinations about the eye 106 in eyes that have smaller than average pupil diameters such as, for example, approximately 2 mm or less. This is currently a challenge for many photorefractors that require assessing the slope of the reflected light over a wide pupil diameter, making it is less useful in more brightly lit rooms or in older patients who have smaller pupils. Further, embodiments of the apparatus described herein can monitor the reflected light in just the center region of the pupil in this measurement allowing accurate measurement of the smaller pupil.

Further, embodiments of the apparatus described herein can monitor the reflected light in a natural pupil or an artificial pupil. An artificial, or second pupil can be optically created for an eye by combining lenses and apertures, without placing anything inside the eye. Vision scientists regularly create what is called a Maxwellian View during experiments where they want to give all subjects the same pupil size by creating an artificial pupil. An artificial pupil could be optically created or physically created by placing an aperture in front of the eye.

Alternatively or optionally, the apparatus 100 as described herein can be used to make a determination of the subject's left eye or right eye. Similarly, it can be used to make a determination of the subject's left eye and right eye.

Though not shown in FIG. 1, the apparatus 100 can optionally include a light meter or any other mechanism for measuring ambient lighting levels. The light meter can detect an intensity for the ambient light conditions and provide an indication if the ambient light conditions are too low for the apparatus 100 to capture an image of the eye of the subject based upon the reflected ambient light. In another aspect, the light meter can measure ambient lighting conditions and such measurement can be used to adjust the image or the calculation of refractive error using regression analysis accordingly.

In some instances, calibration factors are determined to assist in identifying a color temperature of the ambient lighting in which the image of the eye of the subject is obtained. The processor 104 can further execute computer-readable instructions stored on the memory 108 to determine a color temperature of the ambient lighting. The determined color temperature of the ambient lighting is used to adjust the factors for making the determination about the eye 106. For example, the determined color temperature of the ambient lighting can be used by the processor when making a determination about the eye based at least in part on the overall brightness or intensity of the pixels (e.g., red, green, blue) that comprise the reflected ambient light as determined from the image acquired by the sensor 102 or as determined based on reflected ambient light using the sensor 102.

In some instances, the calibration factors can be determined by the processor using the sclera and/or pupil of the eye 106. For example, pixels and/or reflections from the sclera and/or pupil of the image of the eye can be used to sense the color temperature of the ambient lighting and then an algorithm that is formulated for that lighting color temperature is used to make a determination about the eye 106. In effect, the sclera and/or pupil is used as a white balance for determining a color temperature. In some instances, the determination about the eye is based at least in part on the overall brightness or intensity of the red, green and blue pixels that comprise the reflected ambient light as determined from the image acquired by the sensor 102 and as such overall brightness and/or intensity is adjusted based on the determined ambient color temperature.

Alternatively, reflections from the sclera and/or pupil of the eye of the subject can be acquired and used in real-time by the processor 104 to sense the color temperature of the ambient lighting and adjust the algorithm. In some instances, hue and/or luminance of the sclera can be used by the sensor 102 and associated processor 104 to determine the color temperature of the ambient lighting and adjust the algorithm.

Alternatively and/or optionally, an external white balance card can be used by the processor 104 as a calibration factor when determining the color temperature of the ambient lighting. Similar to the above, the determined color temperature can be used when making determinations about the eye include an autorefraction or a photorefraction measurement such as calculating refractive error.

In some instances, when an image of the sclera is captured using a device such as a smartphone having a camera, the camera may be located (e.g., in the upper left corner of the back of the phone) such that when images of the eye are being captured, the body of the smartphone casts a shadow on the sclera that is to the right of the iris in the image (not the patient's right; would be patient's left). So, in these instances, to use the sclera as a white balance, it is better to use the sclera to the left of the iris.

Figure 3:
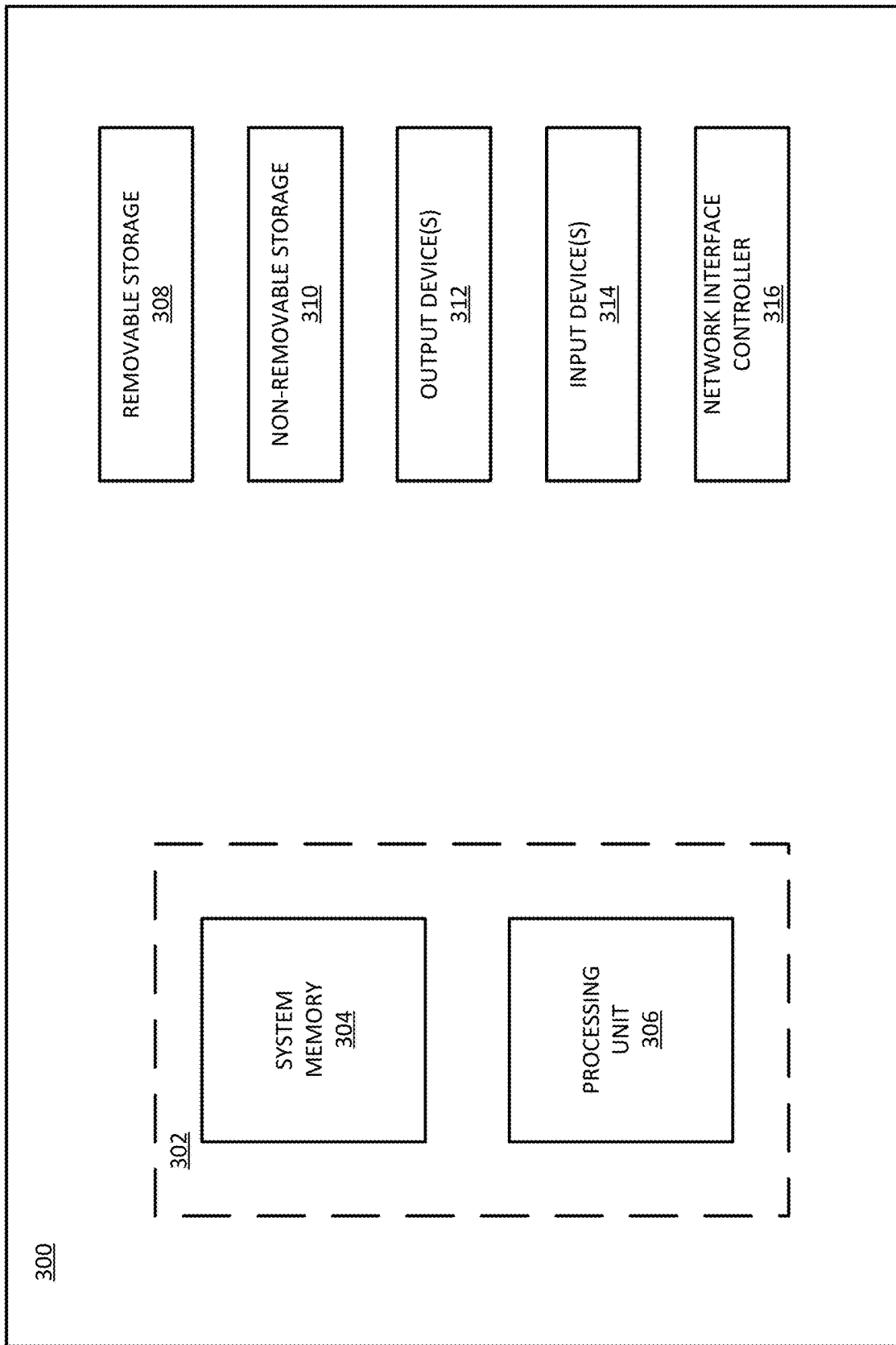
FIG. 3 illustrates an example computing device upon which embodiments of the invention may be implemented.

When the logical operations described herein are implemented in software, the process may execute on any type of computing architecture or platform. Such a computing device 300 as shown in FIG. 3 can be the same as computing device 110, described above, or used alternatively for computing device 110. For example, referring to FIG. 3, an example computing device 300 upon which embodiments of the invention may be implemented is illustrated. The computing device 300 can optionally be a mobile computing device such as a laptop computer, a tablet computer, a mobile phone and the like. The computing device 300 may include a bus or other communication mechanism for communicating information among various components of the computing device 300. In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Computer-readable media refers to any media that is capable of providing data that causes the computing device 300 (i.e., a machine) to operate in a particular fashion. Various computer-readable media may be utilized to provide instructions to the processing unit 306 for execution. Common forms of computer-readable media include, for example, magnetic media, optical media, physical media, memory chips or cartridges, or any other non-transitory medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

Computing device 300 typically includes a variety of computer-readable media. Computer-readable media can be any available media that can be accessed by device 300 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 304, removable storage 308, and non-removable storage 310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 300. Any such computer storage media may be part of computing device 300.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

The techniques for making a determination about an eye in ambient lighting conditions described herein can optionally be implemented with a mobile computing device, such as a laptop computer, tablet computer or mobile phone. Accordingly, the mobile computing device is extremely small compared to conventional devices and is very portable, which allows the mobile computing device to be used wherever needed. Many conventional devices have a chin rest that requires the subjects to only look straight ahead during this testing. Unlike conventional devices, the mobile computing device can be placed in any position relative to the subject's head where the eyes can still be viewed and measurements can be made.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. FIG. 4 illustrates an example method for making a determination about an eye of a subject based upon ambient light reflected out of the eye. The method comprises step 402, determining, using a computing device, a color temperature of ambient lighting, as described herein. Step 404, detecting, using the computing device, ambient light reflected out of an eye of a subject from a retina of the eye of the subject; and step 406, making a determination about the eye of the subject based upon the reflected ambient light, wherein the reflected ambient light is adjusted by the computing device based on the determined color temperature of the ambient lighting.

Making the determination about the eye of the subject based upon the reflected ambient light comprises making a determination based at least in part on an aspect of the reflected ambient light. The aspects can include making a determination based at least in part on an overall brightness (luminescence) of an image of the eye and the intensity of one or more colors of the reflected ambient light. Consider one non-limiting example where the determination about the eye of the subject comprises refractive error and the refractive error is determined by a formula developed through regression analysis. The example formula considers overall brightness ("LuminancePupil") of the pupil from the image capture using only ambient light and the intensity of blue from one or more pixels from the pupil in the image ("BluePixel"), the intensity of red in one or more pixels from the pupil in the image ("RedPixel"), and the intensity of green in one or more pixels from the pupil in the image ("GreenPixel") while controlling for ambient light levels ("LuminanceAmbient"). The example formula comprises: Refractive Error=−36.47+(−638.37*RedPixel)+ (−1807.2*GreenPixel)+(−333.64*BluePixel)+(2156.5*LuminancePupil)+(183.0*LuminanceAmbient)m+ (890.2*GreenPixel*LuminanceAmbient)+ (−4895.0*RedPixel*RedPixel)+ (−8457.1*GreenPixel*GreenPixel)+ (−1711.4*BluePixel*BluePixel)+ (1592.8*LuminancePupil*LuminancePupil)+ (−178.7*LuminanceAmbient*LuminanceAmbient), and has an $R^2$ of approximately 0.78 for fitting the measurement to the intended refractive error of the eye. It is to be appreciated that this is only one example of a formula for making a determination about the eye and other formulas, and types of analysis used for generating predictive formulas, are contemplated within the scope of this disclosure.

Referring back to the method described in FIG. 4, detecting ambient light reflected out of an eye of a subject from a retina of the eye of the subject can further comprise capturing, using a sensor, an image of the eye of a subject, wherein the image is captured using only ambient lighting conditions and wherein non-relevant reflections from the eye of the subject are managed while capturing the image; determining, using the computing device, an overall intensity of light from a plurality of pixels located within at least a portion of a pupil captured in the image; determining, using the computing device, a first intensity of a first color from the plurality of pixels located within at least a portion of a pupil of the eye of the subject captured in the image; determining, using the computing device, a second intensity of a second color from the plurality of pixels located within the at least a portion of the pupil of the eye of the subject captured in the image; and comparing, by the computing device, a relative intensity of the first color and a relative intensity of the second color, wherein the comparison and the overall intensity are used to make the determination about the eye of the subject based upon the reflected ambient light. For example, when the intensity of the first color is brighter relative to the intensity of the second color and an overall intensity is relatively brighter, the determination about the eye of the subject based upon the reflected ambient light comprises a positive value or hyperopia. Conversely, when the intensity of the first color is dimmer relative to the intensity of the second color and an overall pixel intensity is relatively dimmer, the determination about the eye of the subject based upon the reflected ambient light comprises a negative value or myopia. The first color can comprise any one or any combination of red green and blue and the second color can comprise any one or any combination of red, green and blue.

In the method of FIG. 4, the determination about the eye of the subject based upon the reflected ambient light can alternatively or optionally comprise an autorefraction or a photorefraction measurement. Capturing, using the sensor, an image of the eye of the subject can comprise capturing a first image using only ambient lighting conditions with the sensor through a spectacle lens or a contact lens while the subject is wearing the spectacle lens or the contact lens over the eye and capturing a second image using only ambient lighting conditions with the sensor while the subject is not wearing the spectacle lens or the contact lens over the eye and the aspects of the reflected ambient light in the first image can be compared to the aspects of the reflected ambient light in the second image and the determination about the eye of the subject based upon the reflected ambient light is based on the comparison and comprises an estimated prescription for the spectacle lens or the contact lens.

The method shown in FIG. 4 can further comprise making a first determination about the eye of the subject based upon the reflected ambient light from a first plurality of pixels located within the portion of the pupil of the eye of the subject captured in the image; making a second determination from a second plurality of pixels located within the portion of the pupil of the eye of the subject captured in the image, wherein the second plurality of pixels are a subset of the first plurality of pixels; making a third determination from a third plurality of pixels located within the portion of the pupil of the eye of the subject captured in the image, wherein the third plurality of pixels are a subset of the first plurality of pixels and are separate from the second plurality of pixels; and comparing the first determination, the second determination and the third determination to make the determination about the eye of the subject based upon the reflected ambient light. Comparing the first determination, the second determination and the third determination to make the determination about the eye of the subject based upon the reflected ambient light can comprise one or more of determining a standard deviation of the first determination to the second determination, a standard deviation of the first determination to the second determination, or a standard deviation of the second determination to the third determination, wherein the determined standard deviation indicates the determination about the eye of the subject based upon the reflected ambient light. For example, the determination about the eye of the subject based upon the reflected ambient light can be the presence or the absence of astigmatism. When the presence of astigmatism is detected, an amount of astigmatism can be determined by comparing the overall intensity and the relative intensity of the first color or the relative intensity of the second color of various regions of the pupil. Such measurements of various regions of the pupil can comprise measuring one or more of hyperopia or myopia at the various regions of the pupil.

As noted above, the method of FIG. 4 can include managing non-relevant reflections from the eye while capturing the image, which can comprise managing reflections from a cornea or a lens of the eye of the subject while capturing the image. For example, a polarizing filter can be placed over a lens of the sensor or between the sensor and the eye of the subject. Managing non-relevant reflections from the eye while capturing the image can also comprise blocking light that would lead to reflections from a corneal surface of the eye or a lens of the eye. For example, a surface can be provided that absorbs light or prevents the non-relevant reflections from the eye while capturing the image. In one aspect, the surface can have a black matte finish. In various aspects the surface can comprise a portion of the sensor or at least a portion of a case that houses the sensor.

FIG. 5 illustrates an alternate example method for making a determination about an eye of a subject based upon ambient light reflected out of the eye. The method comprises step 502, capturing, using a sensor, an image of an eye of a subject, wherein said image is captured using only ambient lighting conditions and wherein non-relevant reflections from a cornea and a lens of the eye of the subject are managed while capturing the image. At step 504, an average red intensity can be determined from a plurality of pixels located within at least a portion of a pupil captured in the image. At step 506, an average blue intensity is determined from the plurality of pixels located within the at least a portion of a pupil captured in the image. At step 508, an overall intensity is determined of the plurality pixels located within the at least a portion of a pupil captured in the image; and, at step 510, compare the average red intensity and the average blue intensity, wherein the comparison and the determined overall intensity are used to determine an optical quality of the eye.

In the method of FIG. 5, the determination about the eye of the subject based upon the reflected ambient light can alternatively or optionally comprise an autorefraction or a photorefraction measurement. Capturing, using the sensor, an image of the eye of the subject can comprise capturing a first image using only ambient lighting conditions with the sensor through a spectacle lens or a contact lens while the subject is wearing the spectacle lens or the contact lens over the eye and capturing a second image using only ambient lighting conditions with the sensor while the subject is not wearing the spectacle lens or the contact lens over the eye and the aspects of the reflected ambient light in the first image can be compared to the aspects of the reflected ambient light in the second image and the determination about the eye of the subject based upon the reflected ambient is based on the comparison and comprises an estimated prescription for the spectacle lens or the contact lens.

The method shown in FIG. 5 can further comprise determining a presence or an absence of astigmatism. If the presence of astigmatism is indicated, an amount of astigmatism can be determined by comparing optical quality measurements of various regions of the pupil. Such optical quality measurements of various regions of the pupil can comprise measuring one or more of hyperopia or myopia at the various regions of the pupil.

As noted above, the method of FIG. 5 can include managing non-relevant reflections from the eye while capturing the image, which can comprise managing reflections from a cornea or a lens of the eye of the subject while capturing the image. For example, a polarizing filter can be placed over a lens of the sensor or between the sensor and the eye of the subject. Managing non-relevant reflections from the eye while capturing the image can also comprise blocking light that would lead to reflections from a corneal surface of the eye or a lens of the eye. For example, a surface can be provided that absorbs light or prevents the non-relevant reflections from the eye while capturing the image. In one aspect, the surface can have a black matte finish. In various aspects the surface can comprise a portion of the sensor or at least a portion of a case that houses the sensor.

FIG. 6 is a flowchart for a method of making a determination about an eye of a subject based upon ambient light reflected out of the eye. The method comprises 602, determining, using a computing device, a color temperature of ambient lighting. In some instances, determining the color temperature of ambient lighting comprises determining, by the computing device, the color temperature of the ambient lighting using the sclera and/or pupil of the eye of the subject, wherein reflected light of the sclera and/or pupil of the eye is sensed by the sensor. In some instances, determining the color temperature of the ambient lighting using the sclera and/or pupil of the eye of the subject comprises using reflected light from the sclera and/or pupil of the eye to sense the color temperature of the ambient lighting. In some instances, determining the color temperature of the ambient lighting using the sclera and/or pupil of the eye of the subject comprises acquiring, in real-time, reflected light from the sclera and/or pupil of the eye that are used by the computing device to sense the color temperature of the ambient lighting. In some instances, the color temperature of the ambient lighting using the sclera and/or pupil of the eye of the subject comprises determining, by the computing device, a hue and/or luminance of the sclera of the eye of the subject and the computing device using the hue and/or luminescence to determine the color temperature of the ambient lighting. In some instances, determining the color temperature of ambient lighting comprises determining, by the computing device, the color temperature of the ambient lighting using an external white balance card wherein reflected light from the white balance card is sensed by the sensor.

At 604, reflected ambient light out of an eye of a subject from a retina of the eye of the subject is detected. In one aspect the detecting comprises sensing, using a sensor, at least a portion of the eye of the subject, wherein the sensing is performed using only ambient lighting conditions and wherein non-relevant reflections from the eye of the subject are managed while sensing the portion of the eye, and wherein the sensed portion of the eye comprises at least a portion of a pupil of the eye of the subject. In some instances, sensing, using the sensor, the portion of the eye of the subject comprises sensing at a first time through a spectacle lens or a contact lens while the subject is wearing the spectacle lens or the contact lens over the eye and sensing at a second time while the subject is not wearing the spectacle lens or the contact lens over the eye and the first sensing information is compared to the second sensing information and the determination about the eye of the subject based upon the reflected ambient light is based on the comparison and comprises an estimated prescription for the spectacle lens or the contact lens. In some instances, managing non-relevant reflections from the eye while capturing the image comprises managing reflections from a cornea or a lens of the eye of the subject while sensing the eye. In other instances, managing non-relevant reflections from the eye while sensing the eye comprises placing a polarizing filter over a lens of the sensor or between the sensor and the eye of the subject, or wherein managing non-relevant reflections from the eye while sensing the eye comprises blocking light that would lead to reflections from a corneal surface of the eye or a lens of the eye, or wherein managing non-relevant reflections from the eye while sensing the eye comprises providing a surface that absorbs light or prevents the non-relevant reflections from the eye while sensing the eye.

At 606, an overall intensity of light from the reflected ambient light from the sensed portion of the pupil of the eye of the subject is determined. At 608, the overall intensity of light is adjusted by the computing device based on the determined color temperature of the ambient lighting. At 610, a first intensity of a first color from the reflected ambient light from the sensed portion of the pupil of the eye of the subject is determined. At 612, the first intensity of the first color is adjusted by the computing device based on the determined color temperature of the ambient lighting. At 614, a second intensity of a second color from the reflected ambient light from the sensed portion of the pupil of the eye of the subject is determined. In some instances, the first color comprises any one or any combination of red, green, and blue and the second color comprises any one or any combination of red, green, and blue. At 616, the second intensity of the second color is adjusted by the computing device based on the determined color temperature of the ambient lighting. At 618, a relative intensity of the first color and a relative intensity of the second color are compared, and at 620 a determination about the eye of the subject is made based upon the reflected ambient light, where the comparison and said overall intensity are used to make the determination about the eye of the subject based upon the reflected ambient light.

In some instances, the first intensity of the first color is brighter relative to the second intensity of the second color and the overall intensity is relatively brighter in luminescence than a myopic eye, and the determination about the eye of the subject based upon the reflected ambient light comprises a positive value or hyperopia.

In some instances, the first intensity of the first color is dimmer relative to the second intensity of the second color and the overall intensity is relatively dimmer in luminescence than a myopic eye, and the determination about the eye of the subject based upon the reflected ambient light comprises a negative value or myopia.

In some instances, the determination about the eye of the subject based upon the reflected ambient light comprises an autorefraction or a photorefraction measurement.

In some instances, the method may further comprise making a first determination about the eye of the subject based upon the reflected ambient light from a first portion of the sensed pupil of the eye; making a second determination from a second portion of the sensed pupil of the eye of the subject, wherein the second portion of the sensed pupil is a subset of the first portion of the sensed pupil of the eye; making a third determination from a third portion of the sensed pupil of the eye of the subject, wherein the third portion of the pupil is a subset of the first portion of the sensed pupil of the eye and is separate from the second sensed portion of the eye; comparing the first determination, the second determination and the third determination to make the determination about the eye of the subject based upon the reflected ambient light. In some instances, comparing the first determination, the second determination and the third determination to make the determination about the eye of the subject based upon the reflected ambient light comprises one or more of determining a standard deviation of the first determination to the second determination, a standard deviation of the first determination to the third determination, or a standard deviation of the second determination to the third determination, wherein the determined standard deviation indicates the determination about the eye of the subject based upon the reflected ambient light. In some instances, the determination about the eye of the subject based upon the reflected ambient light is a presence or an absence of astigmatism. In some instances, the presence of astigmatism is detected and an amount of astigmatism is determined by comparing the overall intensity and the relative intensity of the first color or the relative intensity of the second color of various regions of the pupil.

As used herein, at least one of the subject's eyes can be the subject's left eye or right eye. Alternatively, at least one of the subject's eyes can be the subject's left eye and right eye. This disclosure contemplates that the optical qualities based on the subject's left eye and right eye can be the same or different.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method comprising:
   determining, using a computing device, a color temperature of ambient lighting;
   detecting, using the computing device, reflected ambient light out of an eye of a subject from a retina of the eye of the subject, wherein said detecting comprises:
      sensing, using a sensor, at least a portion of the eye of the subject, wherein said sensing is performed using only ambient lighting conditions and wherein non-relevant reflections from the eye of the subject are managed while sensing the portion of the eye, and wherein the sensed portion of the eye comprises at least a portion of a pupil of the eye of the subject;
      determining, using the computing device, an overall intensity of light from the reflected ambient light from the sensed portion of the pupil of the eye of the subject, wherein the overall intensity of light is adjusted by the computing device based on the determined color temperature of the ambient lighting;
      determining, using the computing device, a first intensity of a first color from the reflected ambient light from the sensed portion of the pupil of the eye of the subject, wherein the first intensity of the first color is adjusted by the computing device based on the determined color temperature of the ambient lighting;
      determining, using the computing device, a second intensity of a second color from the reflected ambient light from the sensed portion of the pupil of the eye of the subject, wherein the second intensity of the second color is adjusted by the computing device based on the determined color temperature of the ambient lighting;
      comparing, by the computing device, a relative intensity of the first color and a relative intensity of the second color; and
   making a determination about the eye of the subject based upon the reflected ambient light, wherein said comparison and said overall intensity are used to make the determination about the eye of the subject based upon the reflected ambient light.

2. The method of claim 1, wherein sensing, using the sensor, the portion of the eye of the subject comprises capturing, using an image capture device, an image of the eye of the subject, wherein said image is captured using only ambient lighting conditions and wherein non-relevant reflections from the eye of the subject are managed while capturing the image, and wherein the captured image of the eye comprises the portion of a pupil of the eye of the subject;
   wherein the overall intensity of light is determined from a plurality of pixels located within the portion of the pupil of the eye of the subject captured in the image, wherein the overall intensity of light is adjusted by the computing device based on the determined color temperature of the ambient lighting;
   wherein the first intensity of the first color is determined from the plurality of pixels located within the portion of the pupil of the eye of the subject captured in the image, wherein the first intensity of the first color is adjusted by the computing device based on the determined color temperature of the ambient lighting; and wherein the second intensity of the second color is determined from the plurality of pixels located within the portion of the pupil of the eye of the subject captured in the image, wherein the second intensity of the second color is adjusted by the computing device based on the determined color temperature of the ambient lighting.

3. The method of claim 1, wherein the first color comprises any one or any combination of red, green, and blue and the second color comprises any one or any combination of red, green, and blue.

4. The method of claim 1, wherein sensing, using the sensor, the portion of the eye of the subject comprises sensing at a first time through a spectacle lens or a contact lens while the subject is wearing the spectacle lens or the contact lens over the eye and sensing at a second time while the subject is not wearing the spectacle lens or the contact lens over the eye and the first sensing information is compared to the second sensing information and the determination about the eye of the subject based upon the reflected ambient light is based on the comparison and comprises an estimated prescription for the spectacle lens or the contact lens.

5. The method of claim 1, wherein the first intensity of the first color is brighter relative to the second intensity of the second color and the overall intensity is relatively brighter in luminescence than a myopic eye, and the determination about the eye of the subject based upon the reflected ambient light comprises a positive value or hyperopia.

6. The method of claim 1, wherein the first intensity of the first color is dimmer relative to the second intensity of the second color and the overall intensity is relatively dimmer in luminescence than a myopic eye, and the determination about the eye of the subject based upon the reflected ambient light comprises a negative value or myopia.

7. The method of claim 1, wherein the method further comprises:
making a first determination about the eye of the subject based upon the reflected ambient light from a first portion of the sensed pupil of the eye;
making a second determination from a second portion of the sensed pupil of the eye of the subject, wherein the second portion of the sensed pupil is a subset of the first portion of the sensed pupil of the eye;
making a third determination from a third portion of the sensed pupil of the eye of the subject, wherein the third portion of the pupil is a subset of the first portion of the sensed pupil of the eye and is separate from the second sensed portion of the eye;
comparing the first determination, the second determination and the third determination to make the determination about the eye of the subject based upon the reflected ambient light.

8. The method of claim 7, wherein comparing the first determination, the second determination and the third determination to make the determination about the eye of the subject based upon the reflected ambient light comprises one or more of determining a standard deviation of the first determination to the second determination, a standard deviation of the first determination to the third determination, or a standard deviation of the second determination to the third determination, wherein the determined standard deviation indicates the determination about the eye of the subject based upon the reflected ambient light.

9. The method of claim 7, wherein the determination about the eye of the subject based upon the reflected ambient light is a presence or an absence of astigmatism.

10. The method of claim 9, wherein the presence of astigmatism is detected and an amount of astigmatism is determined by comparing the overall intensity and the relative intensity of the first color or the relative intensity of the second color of various regions of the pupil.

11. The method of claim 1, wherein managing non-relevant reflections from the eye while capturing the image comprises managing reflections from a cornea or a lens of the eye of the subject while sensing the eye.

12. The method of claim 1, wherein managing non-relevant reflections from the eye while sensing the eye comprises placing a polarizing filter over a lens of the sensor or between the sensor and the eye of the subject, or wherein managing non-relevant reflections from the eye while sensing the eye comprises blocking light that would lead to reflections from a corneal surface of the eye or a lens of the eye, or wherein managing non-relevant reflections from the eye while sensing the eye comprises providing a surface that absorbs light or prevents the non-relevant reflections from the eye while sensing the eye.

13. The method of claim 1, wherein the subject's pupil has a diameter of approximately 2 mm or less.

14. The method of claim 1, wherein the subject's pupil is a natural pupil or the subject's pupil is an artificial pupil.

15. The method of claim 1, wherein the determination about the eye of the subject based upon the reflected ambient light comprises an autorefraction or a photorefraction measurement.

16. The method of claim 1, wherein determining, using the computing device, the color temperature of ambient lighting comprises determining, by the computing device, the color temperature of the ambient lighting using the sclera and/or pupil of the eye of the subject, wherein reflected light of the sclera and/or pupil of the eye is sensed by the sensor.

17. The method of claim 16, wherein determining, by the computing device, the color temperature of the ambient lighting using the sclera and/or pupil of the eye of the subject comprises using reflected light from the sclera and/or pupil of the eye to sense the color temperature of the ambient lighting.

18. The method of claim 16, wherein determining, by the computing device, the color temperature of the ambient lighting using the sclera and/or pupil of the eye of the subject comprises acquiring, in real-time, reflected light from the sclera and/or pupil of the eye that are used by the computing device to sense the color temperature of the ambient lighting.

19. The method of claim 16, wherein determining, by the computing device, the color temperature of the ambient lighting using the sclera and/or pupil of the eye of the subject comprises determining, by the computing device, a hue and/or luminance of the sclera of the eye of the subject and the computing device using the hue and/or luminescence to determine the color temperature of the ambient lighting.

20. The method of claim 1, wherein determining, using the computing device, the color temperature of ambient lighting comprises determining, by the computing device, the color temperature of the ambient lighting using an external white balance card wherein reflected light from the white balance card is sensed by the sensor.

* * * * *